United States Patent
Treiber et al.

(12) 
(10) Patent No.: US 6,177,008 B1
(45) Date of Patent: *Jan. 23, 2001

(54) DUAL COMPARTMENT SOLID PHASE EXTRACTION CARTRIDGE

(75) Inventors: Laszlo R. Treiber, Chester; Ali Shafiee, Westfield, both of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/190,503

(22) Filed: Nov. 12, 1998

Related U.S. Application Data

(63) Continuation of application No. 08/901,041, filed on Jul. 25, 1997, now abandoned.
(60) Provisional application No. 60/022,921, filed on Aug. 1, 1996.

(51) Int. Cl.$^7$ ................................................ B01D 15/08
(52) U.S. Cl. ........................................ 210/198.2; 210/656
(58) Field of Search ............................ 210/635, 656, 210/198.2, 282; 96/101; 422/70

(56) References Cited

U.S. PATENT DOCUMENTS

| | | | |
|---|---|---|---|
| 2,487,574 | * 11/1949 | Meng | 210/198.2 |
| 3,487,938 | * 1/1970 | Patterson | 210/198.2 |
| 3,511,377 | * 5/1970 | Hadina | 210/198.2 |
| 3,791,522 | * 2/1974 | Eisenbeiss | 210/198.2 |
| 4,093,550 | * 6/1978 | Stahl | 210/198.2 |
| 4,131,547 | * 12/1978 | Michel | 210/198.2 |
| 4,187,177 | * 2/1980 | Stahl | 210/198.2 |
| 4,214,993 | 7/1980 | Forsythe, Jr. et al. | 210/282 |
| 4,270,921 | * 6/1981 | Graas | 210/198.2 |
| 4,283,280 | * 8/1981 | Brownlee | 210/198.2 |
| 4,341,635 | 7/1982 | Golias | 210/656 |
| 4,399,032 | 8/1983 | Mott | 210/198.2 |
| 4,451,363 | * 5/1984 | Brownlee | 210/198.2 |
| 4,469,597 | 9/1984 | Mott | 210/198.2 |
| 4,551,249 | * 11/1985 | Shackelford | 210/198.2 |
| 4,554,071 | * 11/1985 | Ruijten | 210/198.2 |
| 4,737,284 | * 4/1988 | Haake | 210/198.2 |
| 4,740,306 | * 4/1988 | Litwack | 210/198.2 |
| 4,758,340 | * 7/1988 | Marchand | 210/198.2 |
| 4,787,971 | 11/1988 | Donald | 210/198.2 |
| 4,806,238 | * 2/1989 | Sattler | 210/198.2 |
| 4,820,276 | 4/1989 | Moreno | 604/190 |
| 4,888,112 | * 12/1989 | Kronwald | 210/198.2 |
| 4,891,133 | 1/1990 | Colvin, Jr. | 210/198.2 |
| 4,956,298 | 9/1990 | Diekmann | 430/311 |
| 5,186,839 | 2/1993 | Kimura et al. | 210/656 |
| 5,188,730 | * 2/1993 | Kronwald | 210/198.2 |
| 5,238,556 | * 8/1993 | Shirkhan | 210/198.2 |
| 5,266,193 | 11/1993 | Kimura et al. | 210/198.2 |
| 5,336,412 | 8/1994 | Huse et al. | 210/635 |
| 5,338,448 | * 8/1994 | Gjerde | 210/198.2 |
| 5,360,544 | * 11/1994 | Nakaso | 210/198.2 |
| 5,378,359 | 1/1995 | Huse et al. | 210/198.2 |
| 5,378,360 | 1/1995 | Huse et al. | 210/198.2 |
| 5,413,708 | 5/1995 | Huse et al. | 210/198.2 |
| 5,439,593 | 8/1995 | Price | 210/660 |
| 5,582,723 | 12/1996 | Boone et al. | 210/198.2 |
| 5,693,223 | * 12/1997 | Yamada | 210/198.2 |

OTHER PUBLICATIONS

Snyder, Introduction to Modern Liquid Chromatography, John Wiley & Sons, 1979, p. 181–182.*

* cited by examiner

Primary Examiner—Ernest G. Therkorn
(74) Attorney, Agent, or Firm—Elliott Korsen; Mark R. Daniel

(57) ABSTRACT

There is disclosed a dual compartment solid phase extraction cartridge comprising a container divided into a top volume and a bottom volume by a porous filter or frit, the top and bottom volumes having a quantity of sorbent. The cartridge is useful in the separation of components of a liquid and solid mixture.

4 Claims, 1 Drawing Sheet

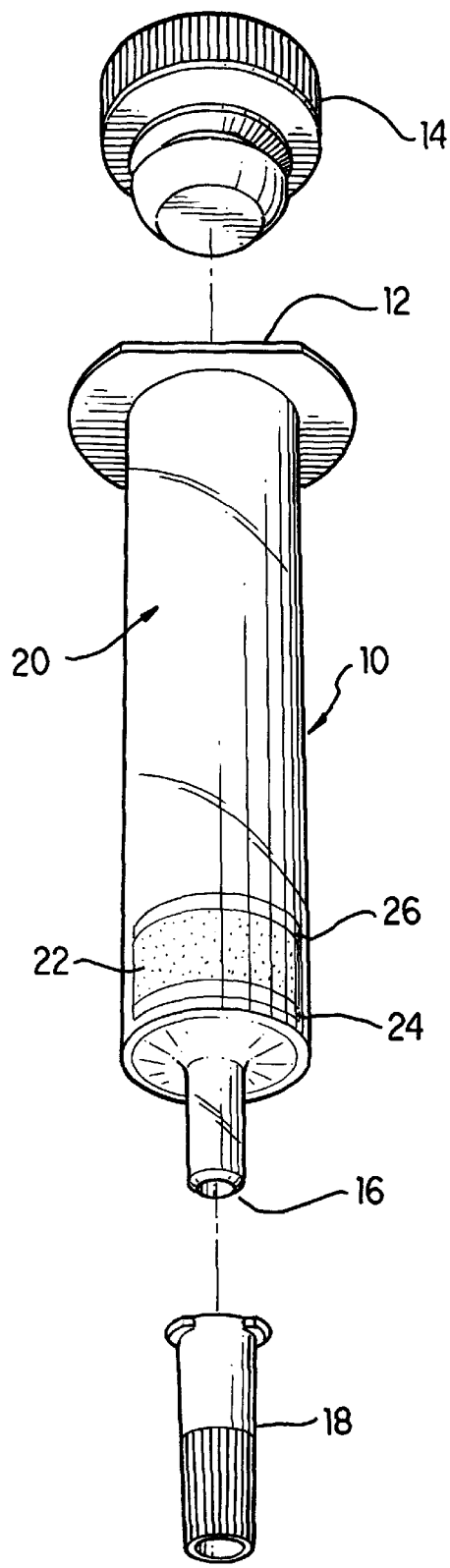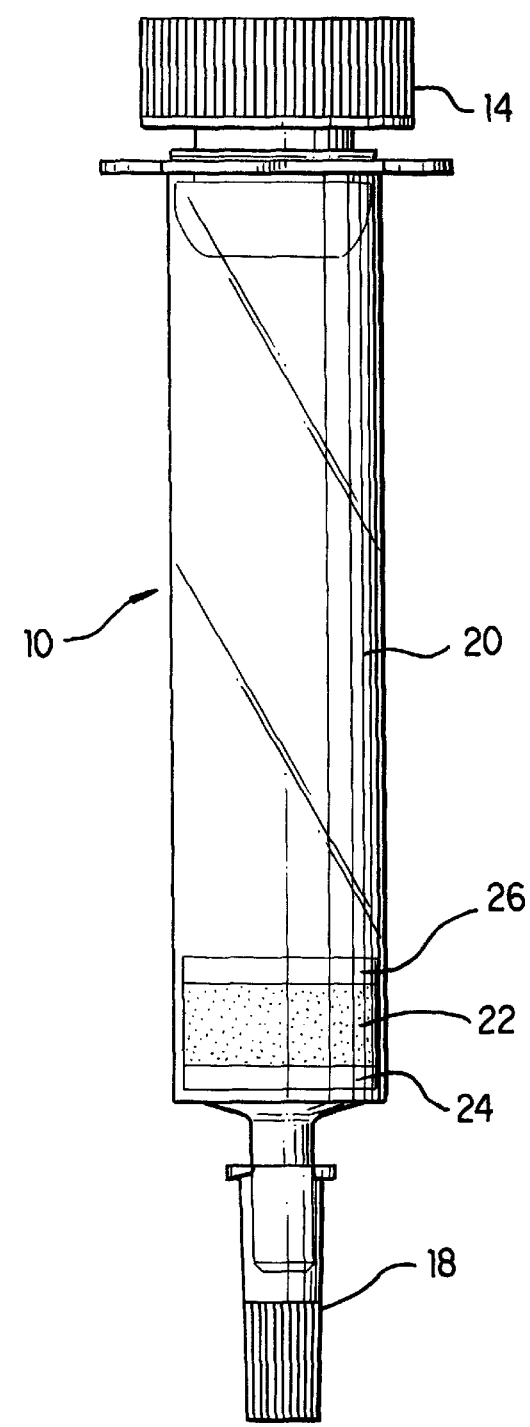
FIG. 1
FIG. 2

DUAL COMPARTMENT SOLID PHASE EXTRACTION CARTRIDGE

This application is a continuation of Ser. No. 08/901,041, filed Jul. 25, 1997, now abandoned, which, in turn, claims priority from Provisional Application No. 60/022,921, filed Aug. 1, 1996.

BACKGROUND OF THE INVENTION

Liquid chromatography provides a means for separating the contents of a liquid sample based upon the polarity, solubility and mobility of the individual components. Within the past twenty years, high performance liquid chromatography (HPLC) has revolutionized the world of analytical chemistry by providing highly efficient columns and packing materials which allow for the separation of very closely related components of a liquid sample.

One drawback to either conventional liquid chromatography or HPLC has been that all samples must be completely dissolved before being applied to the column for separation. Any particulate material which reaches the sorbent or solid phase packing material may adversely effect the flow rate through the column and separation power of the packing and ultimately result in repacking the column or in the case of HPLC, disposal of the column and packing.

To prevent the inadvertent destruction of the packing material, filters or frits or guard columns have been placed at the head of the column which are designed to trap particulate matter which may inadvertently be injected. However, these filters and guard columns are known to clog necessitating extensive cleaning procedures or replacement. Thus, samples which contain partially dissolved material such as cell residue, mycelia, tissue homogenate, debris, etc., must be clarified before being placed on the column.

Several attempts have been made to circumvent the problems presented by the presence of particulate matter in a sample.

For example, simple filtration is often effective if the components of interest can be completely dissolved in the solvent used to prepare the sample. However, simple filtration is not an option when the analyte cannot be completely dissolved away from insoluble materials, such as biological samples where cell fragments may retain some of the material of interest.

In order to overcome this problem, techniques have been developed which involve multiple extraction of the samples and subsequent evaporation of the extract to dryness, followed by redissolution of the sample and finally separation of the resultant particle free solution using a solid phase extraction cartridge or by direct injection onto a chromatography column. The vigorous pre-treatment of the sample, to assure that any undissolved matter is first removed, is time consuming and costly.

A standard solid phase extraction cartridge, such as those manufactured and sold commercially by Applied Separations, Inc., Diazem™ Corporation, EM Science (a division of EM Industries, Inc.), Keystone Scientific, Inc., United Chemical Technologies, Inc., Waters Corporation, Whatman® Inc., Worldwide Monitoring®, YMC, Inc. and many others is commonly used in this procedure. These devices consist of a column having a porous frit or filter which divides the column into a top and bottom section, where the bottom section contains a sorbent such as silica particles which are chemically reacted so that their surface contains various organic functional groups such as phenyl, octyl, octadecyl, or organic or inorganic polymers. When using these cartridges, a solubilized sample substantially free from particulate matters that could clog the top frit is added to the top section of the column and the liquid is allowed to flow either by gravity, under vacuum or by externally applied gas pressure, through the porous frit and then through the sorbent. As the sample passes through the sorbent, certain solutes are either absorbed or adsorbed onto the sorbent and retained. Various solvents are then used to elute the sorbed material in a sequential manner such that separation based upon polarity, solubility and mobility of the various compounds may be effected. The eluted samples may often be applied to an HPLC column or examined with other analytical techniques with or without further concentration.

While the combined use of the liquid extraction/redissolution technique and solid phase extraction cartridges is effective, it suffers from three major problems. First, the sample applied to the column must be substantially free from particulate matter capable of clogging the frit. Second, there is no assurance that all material in the original sample has been fully extracted from the insoluble matter by means of batchwise extraction methods. Third, the extractions, evaporation and redissolution of the sample introduces several inherent errors which must be considered when interpreting the final results.

Thus, what is needed is a simple economic device and procedure which provides for the separation of components, based on their polarity, solubility and mobility extracted from the original biological sample, according to the principles of counter-current extraction wherein the entire contents of the sample, both liquid and solid, can be treated directly, without clogging the column and with minimum inherent error.

SUMMARY OF THE INVENTION

This invention provides a dual compartment solid phase extraction cartridge useful in the separation of components of a liquid and solid mixture. Features of the invention include a container having an open top end with a fitting stopper and bottom end with a fitting cap; the container being divided into a top volume, or extraction volume, and a bottom volume, or chromatography volume, by a porous filter or frit which functions to retain solid matter from entering the bottom volume of the cartridge, the top and bottom volumes having a quantity of sorbent; a second porous filter or frit being located at the bottom of the cartridge to contain the sorbent in the bottom volume; such that when a liquid and solid mixture is added to the top volume of the cartridge, the sorbent in the top volume mixes with the solid material thus facilitating the flow of the liquid by preventing the solids from clogging the frit while the liquid moves through the filter and through the sorbent of the bottom volume and out of the cartridge.

To effect separation of any solubilized components of the liquid and solid mixture, the sorbent may be silica, chemically treated silica, an ion exchange resin or any other material designed to effect liquid chromatographic separation.

There is also disclosed a method for the initial classification of broths, tissue cultures and tissue homogenates containing cellular material in screening operations while performing essential resolution of various components by eliminating sample constituents interfering with the biological assays.

BRIEF DESCRIPTION OF THE DRAWINGS

A more complete understanding of the present invention and attendant advantages and features thereof will be more readily understood by reference to the following detailed description when considered in conjunction with the accompanying drawings wherein:

FIG. 1 is an exploded view of one embodiment of the invention.

FIG. 2 is a side view of the invention.

DETAILED DESCRIPTION OF THE INVENTION

Reference is made to the drawings wherein like numerals designate corresponding or similar elements throughout the several views. FIG. 1 is an exploded view of the cartridge 1 showing a dual compartment solid phase extraction cartridge useful in the separation of components of a liquid and solid mixture comprising a container 10 having an open top end 12 with a fitting stopper 14 and bottom end 16 with a fitting cap 18; the container 10 being divided into a top volume 20 and a bottom volume 22 by a frit or filter 26 to retain solid matter from entering the bottom volume of the cartridge 1, the top and bottom volumes having a quantity of sorbent; a second frit or filter 24 located at the bottom base of the cartridge to contain the sorbent in the bottom volume 22; such that when a liquid and solid mixture is added to the top volume of the cartridge, the sorbent in the top volume mixes with the solid material while the liquid moves through filter 26 and through the sorbent of the bottom volume, through filter 24 and out of the cartridge.

FIG. 2 shows a non-exploded side view of the cartridge as hereinbefore described.

In this application, the terms sorbent and packing will be used interchangeably.

In a preferred embodiment of this invention, the container 10 is a commercially available solid phase extraction cartridge. These cartridges are generally cylindrical with an open top and tapered bottom, wherein the taper terminates in a tip which allows egress of liquid. In the preferred embodiment, the cartridges contain two porous filters which can be constructed of sintered glass. Alternatively, a porous polymer frit may, also be used. The first filter or frit is placed at the bottom of the cartridge and is used to retain any sorbent which is contained within the cartridge. A portion of sorbent is then placed on top of the filter and a second filter is placed on top of the sorbent which holds the sorbent firmly in place. In the instant invention, a quantity of sorbent is added to the top volume of the cartridge. This sorbent may be the same or different than that used in the bottom volume. Samples containing insoluble compounds and other particulate matter such as mycelia, cells, tissue homogenate and other biological debris are then dispersed in a solvent and charged into the top volume of the cartridge and shaken. In practice, a stopper is applied to the open top and bottom of the cartridge so that the sample can be shaken with the packing material of the top volume before it begins to flow out of the cartridge. The sorbent in the top volume has the dual function of adsorbing or absorbing components from the sample and also favorably altering the consistency of the insoluble material of the sample to facilitate passage of the sample into the bottom volume of the cartridge. The frit or filter does not clog, and also functions as a site where further extraction of the solids, using various solvents, may occur. That is, all of the sample, solids and liquids are exposed to all of the eluting solvents, without clogging the frit or filter.

To effect separation of any solubilized components of the liquid and solid mixture, the sorbent can be silica, chemically treated silica, ion exchange resin, or any other material which is designed to effect liquid chromatographic separation. The sorbent is selected from any media used in or useful for normal phase, reversed phase, ion exchange, ion pair, size exclusion, chiral and affinity chromatography.

The sorbent is chemically composed of inorganic or organic polymers and their chemical and physical modifications. Specific examples include silica-based bonded phases ($C_{18}$, $C_8$, $C_N$, phenyl, cyanopropyl, propylene-diol), natural (e.g. cellulose, starch) and synthetic polymers (e.g. styrene-divinylbenzene copolymers, crosslinked vinyl polymers) and their chemical and physical modifications. For use in this invention, the sorbent diameter ranges from about 20 mm to about 200 mm. The particular packing employed will depend on the type of separation to be effected. In addition, chemically reactive materials and catalytic materials may also be used to pretreat the sample before it is applied to the bottom sorbent or before it leaves the cartridge. Further, ingredients which produce chromophores for use in post cartridge analysis may also be used.

Using this technique, samples which ordinarily require exhaustive extraction, evaporation and redissolution may be applied to the solid phase extraction cartridge directly, without clogging of the porous frit. Since a series of solvents ranging in either increasing or decreasing polarity may then be used to elute the various components of both the liquid and solid portions of the sample, there is a far greater probability that all of the solute will be extracted. In addition, since the sorbent and solvents can be tailored to the separation desired, it is often possible to avoid further separation using HPLC or other chromatographic techniques.

The invention may also be used to separate samples containing peptides and proteins. The samples are added to the top volume of the cartridge and mixed with a solvent and with the sorbent which preferentially absorb or precipitate these materials. Removal of the peptides or proteins at this point makes separation using the sorbent found in the bottom volume of the cartridge possible and clogging of the frit is again avoided. In addition, this technique provides a means to thoroughly extract the precipitated matter and assure that all solute has been transferred to the bottom volume of the cartridge.

This procedure is particularly effective in operations such as microbial screening, natural product screening and metabolic studies where proteins, mycelia, cells, tissue homogenate and other biological debris, including insoluble chemical constituents of the materials being screened, can clog the porous frit or interfere with the sorbent. As the example below indicates, this method may be used for purifying and classifying biological materials such as broths, tissue cultures, tissue homogenates, body fluids, This method comprises the steps of:

(a) adding the prepared sample to the top volume of the dual load solid phase extraction cartridge;

(b) mixing the sample with the sorbent in the top volume of the cartridge; and (c) eluting the contents of the sample.

EXAMPLES

The device and method of the invention are designed to satisfy the needs of initial classification of broths containing cellular material in screening operations while also performing essential resolution of various components by eliminating sample constituents interfering with the biological assays. Specifically, the method presented here allows substantial elimination of lipids and proteins from samples through the separation of polar and nonpolar entities by retention of the latter on a suitable sorbent and by allowing the former to pass through the sorbent. Further separation among the nonpolar components, including lipids, is achieved by means of sequential elution. Based on its simplicity, loading capacity and speed, the invention may be useful for high-throughput screening operations.

Samples obtained as whole broths were mixed with 1–3 volumes of methanol and mixed well. Representative aliquots of the mixture (including mycelia and supernatant) were used as feed for the dual load cartridges. The whole broth-methanol mixture (4.0 ml, 1.0–2.0 ml whole broth equivalent, or "WBE") was charged onto the dual compartment cartridge with 6 mL total volume capacity, containing preparative $C_{18}$ reversed-phase packing (particle size 55–105 $\mu$m, 0.25–0.50 g in the top volume and 0.25 g in the bottom volume of the cartridge) from Waters Corporation. The cartridge was equipped with tips compatible with LUER LOCK® female fittings and capped at the bottom. The cartridge was plugged with the stopper at the top and shaken for 1 min. The flow was started by briefly applying vacuum or nitrogen pressure to the cartridge which was drained by gravity to bed level into a test tube (13×100 mm). The fraction collected was marked "50% methanol", or "66% methanol" or "75% methanol", as appropriate.

Methanol (4.0 ml) was charged onto the cartridge and the eluent was again drained by gravity flow. Vacuum (or pressure) is usually not needed unless complete draining of the cartridge is desired. The fraction collected is marked "methanol". The procedure described above was repeated with acetone (4.0 ml) and the fraction collected was marked "Acetone". If extremely nonpolar bioactive components were anticipated, chloroform, methylene chloride or heptane may then be used and the collection tubes marked accordingly. The polar fractions collected were mixed with methyl ethyl ketone ("MEK") and ethyl acetate ("EtOAc") (1:1, 0.6 volumes) and shaken at room temp. for 5 min. to denature proteins. The samples were centrifuged, and the supernatant was decanted and saved with the sediments discarded.

The solutions obtained were evaporated to dryness in a stream of nitrogen at 35° C. and the dry residues representing 2.0 ml WBE redissolved in the appropriate solvents for bioassay. The $C_{18}$ reversed-phase packing in the top volume of the dual load cartridge, which is shaken with the sample, served two main purposes. First, it mimicked the commonly used hexane extraction of the aqueous methanol phase for the removal of lipids. However, the dual load cartridge eliminated the need for separating liquid layers thus making automation more practical. Second, mixed with the mycelia, the top volume improved the flow of eluent through the cartridge. The same packing in the bottom volume of the cartridge provides the conditions for legitimate chromatography.

Modifications and variations of the present invention are possible in light of the above teachings. It is therefore to be understood that, within the scope of the appended claims, the present invention may be practiced otherwise than as specifically described herein.

What is claimed is:

1. A dual compartment solid phase extraction cartridge useful in the gravity separation of components of a liquid and solid mixture at ambient pressure said cartridge comprising a container having an open top end with a fitting stopper and bottom end with a fitting cap; so that a sample can be shaken with the packing material of a top volume before it begins to flow out of the cartridge; the container being divided into the top volume and a bottom volume by a first porous filter or frit which functions to retain solid matter from entering the bottom volume of the cartridge; the top and bottom volumes having a quantity of sorbent; a second porous filter or frit being located at the bottom of the cartridge to contain the sorbent in the bottom volume; such that when a liquid and solid mixture is added to the top volume of the cartridge, the sorbent in the top volume retains the solid material while the liquid moves through the first filter or frit and through the sorbent of the bottom volume and out of the cartridge.

2. The cartridge of claim 1 wherein the sorbent which is found in the top and bottom volumes is selected from any media useful for normal phase, reversed phase, ion exchange, ion pair, size exclusion, chiral and affinity chromatography.

3. The cartridge of claim 2 wherein the sorbent particle size ranges in diameter from about 20 $\mu$m to about 200 $\mu$m in the top volume and 30 $\mu$m to about 70 $\mu$m in the bottom volume.

4. The cartridge of claim 1 wherein the filter is made of sintered glass or a porous polymer frit.

* * * * *